United States Patent [19]

Niles et al.

[11] Patent Number: 4,689,214

[45] Date of Patent: Aug. 25, 1987

[54] COMPOSITION TO COUNTER BREATH ODOR

[75] Inventors: Hollandra P. Niles, Somerset; Susan Herles, Flemington; Stephen Shymon, Metuchen; Abdul Gaffar, Princeton, all of N.J.

[73] Assignee: Colgate-Palmolive Company, New York, N.Y.

[21] Appl. No.: 836,671

[22] Filed: Mar. 10, 1986

Related U.S. Application Data

[63] Continuation-in-part of Ser. No. 723,786, Apr. 16, 1985, abandoned.

[51] Int. Cl.$^4$ .......................... A61K 7/16; A61K 7/26
[52] U.S. Cl. ....................................... 424/49; 424/58; 424/145; 514/900; 514/901
[58] Field of Search .................... 424/48–58; 426/538

[56] References Cited

U.S. PATENT DOCUMENTS

| 2,180,932 | 6/1939 | Stockelbach | 426/538 |
|---|---|---|---|
| 3,988,432 | 10/1976 | Steltenkamp | 426/538 |
| 4,022,880 | 5/1977 | Vinson et al. | 424/49 |
| 4,082,841 | 4/1978 | Pader | 424/52 |
| 4,100,269 | 7/1978 | Pader | 424/49 |
| 4,138,477 | 2/1979 | Gaffar | 424/49 |
| 4,144,323 | 3/1979 | Lamberti | 424/49 |
| 4,247,572 | 1/1981 | Pickenhasen et al. | 426/538 |
| 4,289,754 | 9/1981 | Dhabhar et al. | 424/49 |
| 4,289,755 | 9/1981 | Dhabhar | 424/49 |
| 4,325,939 | 4/1982 | Shah | 424/49 |
| 4,390,556 | 6/1983 | Krasnobajew | 426/538 |
| 4,390,557 | 6/1983 | Krasnobajew | 426/538 |
| 4,402,989 | 9/1983 | Krasnobajew | 426/538 |

FOREIGN PATENT DOCUMENTS

1311060 3/1973 United Kingdom .

OTHER PUBLICATIONS

McNamara et al., GA. 78#115135A(1973) of FR. Vemande 2,127,005, 17 Nov. 1972, Reodorizing Compositions: (10–2000ppm a–ionone efficiently mask bad odors in mouthsprays, toothpaste), 12 pp.
Arctander (1969) Perfume and Flavor Chemicals I: 1777: Alph-Ionone 1778: Beta-Ionone.
Archtander (1960) Perfume and Flavor Materials of Natural Origin 513–516 Peppermint Oil.
Solis-Faffar et al., Journal of Dental Research, vol. 54, No. 2, pp. 351–357 (1975).

Primary Examiner—Shep K. Rose
Attorney, Agent, or Firm—Robert L. Stone; Murray M. Grill; Herbert S. Sylveste

[57] ABSTRACT

A novel composition to counter by preventing and controlling breath odor containing as the essential agents, a salt which provides zinc ions, and an ionone ketone terpene derivative.

12 Claims, No Drawings

COMPOSITION TO COUNTER BREATH ODOR

This application is a continuation in part of application Ser. No. 723,786, filed Apr. 16, 1985, now abandoned.

This invention relates to novel oral formulations comprising a combination of a salt which provides zinc ions and an ionone ketone derivative as an effective material against breath odor.

The prior art is replete with oral compositions containing zinc salts such as zinc chloride, zinc iodide, zinc fluoride, zinc phenol sulfonate and the like as antiseptic agents, and correctives of oral conditions such as pyorrhea. Zinc chloride has commonly been used in oral formulations for its astringency properties. Zinc phenol sulfonate has been utilized in the prior art dentifrice compositions as an anti-plaque and anti-calculus agent as well as an odor inhibitor of fermentation and putrefaction which occurs in the oral cavity. Compositions in which these soluble zinc salts have been used have had the disadvantages such as leaving an unpleasant astringent taste in the mouth and/or having short-lived efficacy against plaque, and as an odor inhibitor.

Sparingly soluble zinc salts such as zinc citrate have been used in dentifrice formulations to prolong the anti-calculus and anti-plaque effectiveness of the zinc ions due to the slow dissolution of the zinc salts in the saliva.

The reaction product of a zinc compound and polymer has been described in U.S. Pat. No. 4,138,477 as a compound which effectively controls mouth odor. Such control can last a few hours; but generally not overnight.

The use of a zinc complex of a specified diketone as an agent for combating tartar and tooth discoloration is also known, as set forth in German Pat. No. 2,229,466. Thus, it is apparent that zinc compounds are generally known to have deodorizing properties as well as other properties desirable in oral hygiene.

Reodorant terpenes have been described in British Pat. No. 1,311,060. Such terpenes include the ketone terpenes, alpha-ionone and beta-ionone.

It is an object of this invention to provide a synergistic improvement in countering breath odor by incorporating into an oral composition a material comprising a compound which provides zinc ions and ionone.

Another object of instant invention is to provide an oral composition which is synergistically effective in countering breath odor over a prolonged period of time.

In accordance with certain of its aspects, this invention relates to an oral composition consisting essentially of a non-toxic zinc salt in amount which provides at least about 0.01 mg of zinc ions in 1 ml of water and an ionone ketone terpene derivative, the ratio of zinc ions to said ionone ketone terpene derivative being about 1000:1 to 5:1 by weight.

The zinc compounds that provide zinc ions for use in combination with ionone may be any physiologically acceptable zinc salt including the water soluble (including sparingly water soluble) organic and inorganic zinc salts which provide at least about 0.01 mg of zinc ions per ml of water. The water-soluble zinc salts (at least 1% soluble) are preferred, especially the zinc halides and zinc acetate. Among sparingly soluble zinc salts, zinc citrate is preferred. Examples of suitable zinc salts that may be employed include:

| | |
|---|---|
| zinc acetate | zinc fluoride |
| zinc ammonium sulfate | zinc formate |
| zinc bromide | zinc iodide |
| zinc chloride | zinc nitrate |
| zinc chromate | zinc phenol sulfonate |
| zinc citrate | zinc salicylate |
| zinc dithionate | zinc sulfate |
| zinc fluosilicate | zinc gluconate |
| zinc tartarate | zinc succinate |
| | zinc glycerophosphate |

Other zinc salts disclosed in U.S. Pat. No. 4,138,477 having a solubility of at least about 0.01 mg of zinc ions per ml of water are incorporated herein by reference.

The zinc salt is present in amounts which provides about 0.01–5% by weight of zinc ions and preferably about 0.02–1% of zinc ions by weight in the oral composition.

The solubility of the zinc salt to provide zinc ions appears to be a factor in the activity against odor formation. However, the effect is synergistically improved when an ionone terpene ketone is present.

Ionone is a ketone terpene derivative containing one ketonic carbonyl group. The basic ionone formula is $(CH_3)_3C_6H_6CH=CHCOCH_3$. It is available as alpha-ionone (b.p. 120° C.) and beta-ionone (b.p. 135°), both of which are colorless liquids and slightly soluble in water. It is employed in oral compositions in amounts such that the ratio of zinc ions to ionone is about 1,000:1 to 10:1 by weight. Other variants of ionone such as gamma-ionone dihydroionone and alphamethyl ionone may also be employed. Furthermore, as used herein, the term "an ionone ketone derivative" includes isomeric forms of ionones, e.g. irone. It is convenient to employ it in oral compositions in amounts of about 0.0005–1% by weight, preferably about 0.001–1%. Alpha-ionone is preferred.

In British Pat. No. 1,311,060, it was theorized that amelioration of oral malodors by ionone may have occurred due either to an ability to block odor receptor sites in the olfactory epithelium or to low olfactory thresholds for the compound and possibly a combination of both. Regardless of the reason for the effect, however, it is not long-lasting. When reduction in breath odor is evaluated after an overnight sleep period, little, if any, reduction is found. On the other hand, when an ionone is in combination with a salt which provides zinc ions, there are synergistic effects in countering breath odor for a prolonged period.

Aqueous solutions and dispersions of control, placebo and various zinc ion-ionone materials can be tested in an in vitro system and in vivo. In the in vitro test, whole human saliva with L-cysteine as substrate is incubated for 3 hours or overnight at 37° C. in an airtight container. After incubation, the headspace volatile sulfur compound ("VSC", the main cause of offensive breath odor) formation is measured by an instrumental GC-flame photometric technique. Since breath odor has been attributed to the presence of VSC's such as hydrogen sulfide, methyl mercaptan and to a lesser extent, dimethyl sulfide, resulting from putrefactive processes occuring in the oral cavity, the in vitro test provides results comparable to in vivo sensory evaluations.

In vivo tests are done on a panel of randomly equally divided people into two groups, one of which uses a control mouthrinse against the other which uses a test mouthrinse. Initially for one week, each group rinses with its respective mouthrinse for one minute each night before sleep. During the following week, each group rinses with the opposite product.

Baseline breath samples are obtained from each subject in order to evaluate breath during the morning after awakening but without prior brushing, rinsing, eating and drinking. Two breath samples are taken from each subject ten minutes apart during which time the subjects keep their mouths closed.

Aqueous dispersion or solutions of zinc salt-ionone material may be produced by separately adding the zinc salt in a dilute solution, a paste or in the dry state, and the ionone to water. The ionone may be conveniently and preferably included as a component added to a flavoring oil, such as oil of peppermint.

While particularly good results in terms of countering breath odor inhibition are obtained by simply applying the aqueous solutions or dispersions of the zinc salt-ionone material, it is understood that it is within the broader aspect of the invention to incorporate zinc salt and ionone material into oral compositions generally, such as clear or cloudy mouth rinses, mouth sprays and toothpastes, which contain an aqueous oral or dental vehicle, or powders which can be readily dispersed or dissolved in an aqueous vehicle. When the oral composition is a simple solution or a mouth rinse or mouth spray the zinc salt and ionone material is typically dissolved in water and a non-toxic alcohol.

The vehicle in a toothpaste, often referred to as a dental vehicle contains liquids and solids. In general, the liquid comprises water and often a humectant such as glycerine, sorbitol, propylene glycol or polyethylene glycol 400 including suitable mixtures thereof. It is usually advantageous to use a mixture of both water and one or two humectants. The total liquid content is generally about 20–90% by weight of the vehicle. The liquid content of the toothpaste generally includes about 5–40% of water. The preferred humectants are glycerine and sorbitol, for instance in amount of about 10–50% by weight.

When the oral composition is a toothpaste, the dental vehicle contains as a solid portion, a gelling agent. The gelling agent includes alkali metal carboxymethyl cellulose, carrageenans such as viscarin and i-carrageenan, gelatin, starch, glucose, sucrose, polyvinyl pyrollidone, polyvinyl alcohol, gums such as gum tragacanth and gum karaya, hydroxypropyl cellulose, methyl cellulose, carboxyethyl cellulose, sodium alginate, Laponite CP or SP, which are each synthetic inorganic complex silicate clays sold under trademark by Laporte Industries. Ltd., and magnesium aluminum silicate gel as well as mixtures thereof. The solid portion or gelling agent of the vehicle is typically present in amount of about 0.25–10% by weight of the toothpaste and preferably about 0.5–5% by weight. Alkali metal carboxymethyl cellulose includes the lithium, sodium and potassium salts. Sodium carboxymethyl cellulose is preferred.

Any suitable substantially water-insoluble polishing agent may be added to the dental vehicle of a toothpaste. There is a relatively large number of such materials known in the art. Representative materials include, for example, dicalcium phosphate, tricalcium phosphate, insoluble sodium metaphosphate, silica, sodium aluminosilicate (silica containing combined alumina), aluminum hydroxide, magnesium carbonate, calcium carbonate, calcium pyrophosphate, calcium sulfate, bentonite, etc., including suitable mixtures thereof. It is preferred to use the water-insoluble phosphate, sodium metaphosphate and/or a calcium phosphate, such as dicalcium phosphate dihydrate. In general, these polishing agents will comprise a major proportion by weight of the solid ingredients. The polishing agent content is variable, but will generally be up to about 75% by weight of the total composition, generally about 20–75%; although, even lower amounts of polishing agent can be employed.

Any suitable or compatible surface-active or detersive material may be incorporated in the dental vehicle. Such compatible materials are desirable to provide additional detersive, foaming and antibacterial properties depending upon the specific type of surface-active material and are selected similarly. These detergents are water-soluble organic compounds usually, and may be anionic, nonionic, or cationic in structure. It is preferred to use the water-soluble non-soap or synthetic organic detergents usually. Suitable detersive materials are known and include, for example, the water-soluble salts of higher fatty acid monoglyceride monosulfate detergent (e.g., sodium coconut fatty acid monoglyceride monosulfate), higher alkyl sulfates (e.g., sodium lauryl sulfate), alkyl aryl sulfonate (e.g., sodium dodecyl benzene sulfonate), methylcocoyl taurate, higher fatty acid esters of 1,2-dihydroxypropanesulfonate) and the like.

Further detersive materials include the substantially saturated higher aliphatic acyl amides of lower aliphatic amino carboxylic acid compounds, such as those having 12 to 16 carbons in the acyl radical. The amino acid portion is derived generally from the lower aliphatic saturated monoamino carboxylic acids having about 2 to 6 carbons, usually the monocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine, N-lauroyl sarcoside, N-lauroyl sarcosine, and sodium N-lauroyl glycine and alanine. For convenience herein, reference to "amino carboxylic acid compound", "sarcoside", and the like refers to such compounds having a free carboxylic group or the water-soluble carboxylate salts.

Other particularly suitable surface-active materials include nonionic agents such as condensates of sorbitan monostearate with approximately 20 moles of ethylene oxide, condensates of ethylene oxide with propylene glycol ("Pluronics"—Pluronic is a Trade Mark) and castor oil ester (e.g. C remopher EL) and amphoteric agents such as quaternized imidazole derivatives, which are available under the trade mark MIRANOL such and MIRANOL C2M. Cationic surface active germicides and anti-bacterial compounds such as diisobutyl-phenoxyethoxyethyl dimethyl benzyl ammonium chloride, tertiary amines having one fatty alkyl group (of from 12–18 carbon atoms) and two (poly)oxyethylene groups attached to the nitrogen (typically containing a total of from 20 to 50 ethanoxy groups per molecule) and salts thereof with acids, and compounds of the structure:

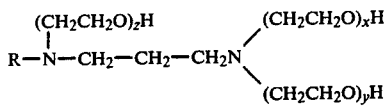

wherein

R is a fatty alkyl group typically containing from 12 to 18 carbon atoms, and x, y and z total 3 or higher, as well as salts thereof with mineral or organic acids, may also be used.

The various surface-active materials may be used in any suitable amount, generally from about 0.05 to about 10% by weight, and preferably from about 0.5 to 5% by weight of the dentifrice composition.

Various other materials may be incorporated in the vehicles of this invention. Examples thereof are preservatives, silicones, chlorophyll compounds, ammoniated materials such as urea, diammonium phosphate and mixtures thereof, materials which can increase contrast with the particles, such as zinc oxide or titanium dioxide and other constituents. These adjuvants are incorporated in the instant compositions in amounts which do not substantially adversely affect the properties and characteristics suitably selected and used in proper amount depending upon the particular type of preparation involved.

Antibacterial agents may also be employed in the vehicles of the instant invention. Typical antibacterial agents include:

$N^1$-(4-chlorobenzyl)-$N^5$-(2,4-dichlorobenzyl)biguanide;
p-chlorophenyl biguanide;
4-chlorobenzhydryl biguanide;
4-chlorobenzhydrylguanylurea;
N-3-lauroxypropyl-N-p-chlorobenzylbiguanide;
1,6-di-p-chlorophenylbiguanide hexane;
1-(lauryldimethylammonium)-8-(p-chlorobenzyl-dimethyl ammonium)octane dichloride;
5,6-dichloro-2-guanidinobenzimidazole;
$N^1$-p-chlorophenyl-$N^5$-laurylbiguanide;
5-amino-1,3-bis(2-ethylhexyl)-3-methylhexahydro pyrimidine;
and their non-toxic acid addition salts.

The antibacterial agent, when present, is employed in amounts of about 0.1–5% by weight, preferably about 0.05–5%.

Any suitable flavoring or sweetening materials may be employed in supplementing the ionone component of the present invention. It is preferable to include the ionone ketpene terpene as an additive to flavoring oil; the presence of flavoring oil improves the taste of the zinc-containing product. Examples of suitable supplemental flavoring oils include oils of spearmint, peppermint, wintergreen, sassafras, clove, sage, eucalyptus, marjoram, cinnamon, lemon and orange, as well as methylsalicylate. Mint oils such as oil of peppermint is most preferred. Suitable sweetening agents include sucrose, lactose, maltose, sorbitol, sodium cyclamate, saccharine, acetosulfam, N-l-α-aspartyl-l-phenvlaniline-methyl ester ("aspartame"), xylitol, chalcone materials. Suitably, flavor and sweetening agent may together comprise from about 0.01 to 5% by weight or more of the compositions of the instant invention, each typically being about 0.005–2.5%. In a typical modification of a flavoring oil such as oil of peppermint which contains about 75% peppermint and the remainder anethole, menthol and/or carvone, about 0.5–1.5% ionone is added thereto. Similar modifications may be made to other flavoring oils.

A fluorine-containing compound having a beneficial effect on the care and hygiene of the oral cavity, e.g., diminution of enamel solubility in acid and protection of the teeth against decay may also be incorporated in the vehicle. Examples thereof include sodium fluoride, stannous fluoride, potassium fluoride, potassium stannous fluoride ($SnF_2$-KF), sodium hexafluorostannate, stannous chlorofluoride, sodium fluorozirconate, and sodium monofluorophosphate. These materials, which disassociate or release fluorine-containing ions in water, suitably may be present in an effective but non-toxic amount, usually within the range of about 0.01 to 1% by weight of the water-soluble fluorine content thereof.

When the oral preparation is a liquid such as mouth rinse or mouth spray which typically contains 20–99% by weight of an aqueous vehicle comprising non-toxic lower aliphatic alcohol, preferably having about 1–30% by weight alcohol such as ethanol, n-propyl, or isopropyl alcohol with the remainder water. Flavor and/or sweetener and surface active agent are also generally present. Mouth sprays also contain a suitable amount of an orally acceptable propellant material such as a fluorocarbon, e.g. Freon on isobutane to propel the spray from a pressurized container.

The oral preparations are typically applied by brushing the teeth with dispersion assisted by saliva in the oral cavity or by rinsing to disperse in the oral cavity for 30–90 seconds at least once daily.

The oral preparations should have a pH practicable for use. The pH range of about 4–9, preferably about 5–7.5, is considered the most practicable for use.

The invention may be practiced and illustrated in accordance with specific embodiments thereof which are described in the following examples. All amounts and proportions set forth in the specification are by weight, unless otherwise indicated.

EXAMPLE 1

Groups of panelists are formed for comparative VSC breath analysis by gas chromatography in combination with a flame photometric detection system according to the procedure described by Solis-Gaffar, Journal of Dental Research, Vol. 54, No. 2, pages 351–357, 1975.

The rinses have formulations A, B, C, and D below.

| PRODUCT FORMULATIONS | | |
|---|---|---|
| Ingredients | A<br>Zinc Chloride<br>Mouth Rinse<br>Percent | C<br>High mint<br>α-ionone<br>with zinc<br>Percent |
| Ethanol | 10.000 | 10.000 |
| Pluronic 108 | 1.000 | 1.000 |
| Sodium saccharin | 0.045 | 0.045 |
| Glycerin | 8.000 | 8.000 |
| Zinc chloride | 0.250 | 0.250 |
| Flavor (Peppermint oil) | 0.218 | 0.218 (including 1% α-ionone) |
| Water (deionized/distilled) | 80.487 | |
| | 100.000 | |
| | D<br>Placebo<br>Mouth<br>Rinse | B<br>High mint<br>α-ionone<br>without<br>zinc |

| PRODUCT FORMULATIONS | | |
|---|---|---|
| Ethanol | 10.000 | 10.000 |
| Pluronic 108 | 1.000 | 1.000 |
| Sodium saccharin | 0.045 | 0.045 |
| Glycerin | 8.000 | 8.000 |
| Flavor (Peppermint Oil) | 0.218 | 0.218 (including 1% α-ionone) |
| Water (deionized/distilled) | 80.737 | |
| | 100.000 | |

These studies are designed as two compartment, single blind and randomized with a cross-over phase. The subjects in each study are randomly assigned to use either the test or placebo rinse. During the cross-over phase each subject switches to the opposite rinse. Each phase consists of two treatments with either the test or placebo rinse. Breath samples are taken the following morning prior to brushing, rinsing, eating and drinking, two samples being taken ten minutes apart. During the period the subjects keep their mouths closed.

The results are summarized in the following table. (Beta-ionone gives similar results to alpha-ionone with and without the presence of zinc): VSC levels are the headspace amounts of the volatile sulfur compounds hydrogen sulfide ($H_2S$), methyl mercaptan ($CH_3SH$) and dimethyl sulfide $(CH_3)_2S$ in incubated putrescent saliva systems measured after overnight incubation in an airtight container by an instrumental GC-flame photometric technique.

The VSC from the mouth air samples have been identified as $H_2S$, $CH_3SH$, and $(CH_3)_2S$. $H_2S$ and $CH_3SH$ account for 90% of the total sulfur volatiles detected instrumentally. Both these compounds have an objectionable putrid odor and the efficacy of the experimental rinse can be measured by its influence on the reduction of these volatiles in the oral cavity. The $(CH_3)_2S$ appeared in small amounts and was not included in the calculations.

TABLE

| Study | Treatment Rinse | No. of Subjects | Duration of Effects | VSC Initial | Final | % Reduction | Significance |
|---|---|---|---|---|---|---|---|
| 1. A. | Zn/Cl₂ | 12 | 3 hours | 13.60 | 10.30 | −24 | 0.05 |
| D. | Placebo | 12 | 3 hours | 13.50 | 11.70 | −13 | N.S. (Not Significant) |
| 2. B. | High Mint/ α-ionone (without zinc) | 15 | overnight | 14.58 | 15.12 | — | N.S. |
| C. | High Mint/α-ionone w/Zinc | 15 | overnight | 15.69 | 7.34 | −53 | 0.001 |
| 3. C. | High Mint/ Zn/α-ionone | 19 | overnight | 16.98 | 9.03 | −46 | 0.001 |
| D. | Placebo | 19 | overnight | 16.45 | 15.95 | 2.57 | N.S. |

The clinical studies that (1) Zinc is effective up to 3 hours (1A); (2) Zinc/high peppermint/α-ionone flavor is effective overnight; high peppermint/α-ionone without zinc is not effective overnight (2C and 3C); and (3) Zinc/high peppermint/α-ionone is significantly more effective than placebo (3). The combinattion of (Zn/high mint is significantly and synergistically more effective than either one by itself.

EXAMPLE 2

The following mouthrinse is prepared for countering breath odors for overnight periods when used immediately before sleep without additional rinsing:

| | PARTS |
|---|---|
| Ethyl alcohol (95%) | 15 |
| *Flavor (high peppermint) | 0.22 |
| Zinc Acetate, dihydrate | 0.40 |
| Sodium saccharin | 0.03 |
| Polyoxyethylene (20) sorbitan Monoisostearate | 2.00 |
| Glycerine | 8.00 |
| Water | Q.S. to 100 |

(Sodium cyclamate may replace sodium saccharin.)
*Flavor Composition

| | PARTS |
|---|---|
| Peppermint | 74.75 |
| Anethole | 9.75 |
| Menthol | 9.75 |
| Carvone | 4.75 |
| α-ionone | 1.00 |

(Each of beta-ionone, dihydroionone and alpha-methyl ionone may replace alpha-ionone.)

EXAMPLE 3

The following toothpaste is prepared for countering breath odors for overnight periods when brushed on teeth and dispersed in the oral cavity immediately before sleep:

| | A PARTS | B PARTS |
|---|---|---|
| Glycerine | 25 | 25 |
| Sodium Carboxymethyl Cellulose | 1.3 | — |
| Hydroxyethyl cellulose | — | 1.0 |
| Sodium Benzoate | 0.50 | 0.50 |
| Sodium Saccharin | 0.20 | 0.20 |
| Titanium Dioxide | 0.40 | 0.40 |
| Zinc chloride | — | 1.00 |
| Zinc Acetate | 1.00 | — |
| Sodium fluoride | — | 0.22 |
| Zeo 49** (Davison) | 29.00 | 29.00 |
| Sodium Laurylsulfate | 1.50 | — |
| Sodium methyl cocovl taurate | — | 1.50 |
| Flavor* | 1.00 | 1.00 |
| Water | Q.S. to 100 | Q.S. to 100 |

*High peppermint plus α-ionone as in Example 1.
**Zeo 49 is a sodium aluminosilicate composed of silica containing about 1% of combined alumina.

EXAMPLE 4

The following mouth spray dispenser is freon propellant is prepared countering breath odors for overnight periods when sprayed into the oral cavity immediately before sleep from a isobutane pressurized container:

|  | Parts |
| --- | --- |
| Sodium Saccidarin | 0.20 |
| Castor Oil Ester (Cremophor E1) | 0.50 |
| Zinc Chloride | 1.00 |
| Alpha-ionone | 0.01 |
| Ethanol | 15.00 |
| Water | Q.S. to 100 |

Although this invention has been described with reference to specific examples, it will be apparent to one skilled in the art that various modifications may be made thereto which fall within its scope.

We claim:

1. An oral synergistic volatile sulfur compound breath-odor controlling aqueous composition consisting essentially of a non-toxic zinc salt and an ionone terpene ketone, the ratio of zinc ions to ionone being about 1000:1 to 5:1 by weight in an aqueous vehicle, said zinc salt being present in amount of about 0.1–5% by weight of zinc ion and said ionone being present in amount of about 0.0005–1% by weight.

2. The oral composition claimed in claim 1 wherein said zinc salt is present in amount which provides about 0.02–1% by weight of zinc ion and said ionone ketone terpene derivative is present in amounts of about 0.001–1% by weight.

3. The oral composition claimed in claim 1 wherein said ionone terpene ketone is selected from the group consisting of alpha-ionone, beta-ionone, gamma-ionone, dihydroionone, alph-methylionone and irone.

4. The oral composition claimed in claim 3 wherein said ionone ketone terpene is alpha-ionone.

5. The oral composition claimed in claim 1 wherein said zinc salt is selected from the group consisting of zinc chloride and zinc acetate.

6. The oral composition and claimed in claim 5 wherein said zinc salt is zinc chloride.

7. The oral composition claimed in claim 1 wherein said vehicle is a dental vehicle containing liquid portion comprising water and a humectant and a solid portion comprising a gelling agent and said oral composition is a toothpaste.

8. The oral composition claimed in claim 1 wherein sid ionone ketone terpene derivatives is present in a component of a flavoring oil in amounts of about 0.5–1% by weight of said flavoring oil.

9. The oral composition claimed in claim 8 wherein said flavoring oil is oil of peppermint which oil of peppermint is present in said oral composition in amounts of about 0.005–2% by weight.

10. The oral composition claimed in claim 1 wherein said vehicle is an aqueous alcohol vehicle wherein said alcohol is a non-toxic lower aliphatic alcohol and said oral preparation is a mouthrinse or mouthspray.

11. A method of synergistically countering volatile sulfur compound breath odor which consists essentially of dispersing in the oral cavity an oral preparation comprising an aqueous vehicle and a zinc salt which provides about 0.01–5% by weight of zinc ions and about 0.0005–1% by weight of ionone ketone terpene derivative the ratio of zinc ions to ionone ketone terpene being about 1000:1 to 5:1 by weight.

12. The method of countering breath odor claims in claim 11 wherein said ionone ketone derivative alpha-ionone and said zinc salt is zinc chloride.

* * * * *